United States Patent [19]

Samour et al.

[11] 3,937,830

[45] Feb. 10, 1976

[54] 5-PIVALOYLOXY-5-(1-PHENYLETHYL) BARBITURIC ACID, ANALGETIC COMPOSITION AND METHOD BASED THEREON

[75] Inventors: Carlos M. Samour, Wellesley; Julius A. Vida, Billerica, both of Mass.

[73] Assignee: The Kendall Company, Walpole, Mass.

[22] Filed: Nov. 22, 1974

[21] Appl. No.: 526,113

Related U.S. Application Data

[63] Continuation of Ser. No. 378,482, July 12, 1973, Pat. No. 3,894,023.

[52] U.S. Cl. .............................................. 424/254
[51] Int. Cl.² ..................................... A61K 31/515
[58] Field of Search .................................. 424/254

Primary Examiner—Stanley J. Friedman

[57] ABSTRACT

5-Pivaloyloxy-5-(1-phenylethyl) barbituric acid, a method of treating symptoms of pain in warm-blooded animals employing said compound and a therapeutic composition containing same are disclosed.

2 Claims, No Drawings

5-PIVALOYLOXY-5-(1-PHENYLETHYL) BARBITURIC ACID, ANALGETIC COMPOSITION AND METHOD BASED THEREON

This is a continuation of application Ser. No. 378,482, filed July 12, 1973, now U.S Pat. No. 3,894,023.

This invention relates to a selected 5-substituted barbituric acid having utility as an analgetic, to a method of treating symptoms of pain in warm-blooded animals employing said analgetic and to a therapeutic composition containing same.

More specifically, this invention relates to 5-pivaloyloxy-5-(1-phenylethyl) barbituric acid, a compound having the formula

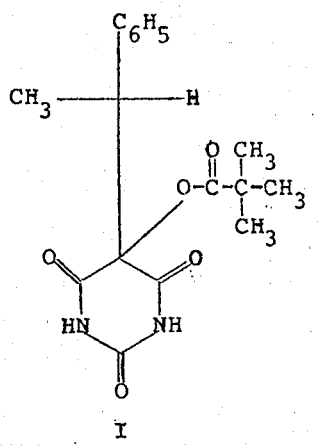

I

Various 5-substituted barbituric acids have been previously prepared and reported in the literature. Thus, U.S Pat. No. 3,464,990 discloses barbituric acids having certain hydroxy phenylalkyl, lower alkoxy phenylalkyl or aralkoxy phenylalkyl substituents, together with hydrogen or a lower alkyl, alkenyl or alkynyl group at the 5-position; these compounds are taught to be useful as tranquilizers. The synthesis of 5-methyl-5-substituted benzyl barbituric acids is reported by J. P. Trivedi and J. J. Trivedi in *Journal Indian Chem. Soc.*, Vol. 35, No. 9, 1958. While no specific therapeutic uses for these compounds are disclosed, the purpose of the synthesis was to prepare compounds which would not have convulsive properties.

Recently it has been found that a series of 5-substituted-5-phenylalkyl barbituric acids have analgetic properties. These compounds, which include compounds having the formula I but having an acyloxy group of 2 to 4 carbon atoms at the 5-position in the barbituric acid ring instead of the pivaloyloxy group of the compound of this invention, are more fully described in Belgian Pat. No. 775,117, granted Nov. 9, 1971.

While the compounds disclosed in the aforementioned Belgian patent are useful analgetics, it has now been found that providing a pivaloyloxy group at the 5-position in the barbituric acid ring markedly enhances the therapeutic index of the compounds. By therapeutic index is meant the $LD_{50}$ of a compound divided by its $ED_{50}$, or the dose required to kill one-half of the test animals divided by the dose required to produce the desired therapeutic effect in one-half of the test animals. It will be apparent that the larger the therapeutic index, the greater the margin of safety and the more desirable the drug.

The compound of this invention is readily prepared by reacting 5-hydroxy-5-(1-phenylethyl) barbituric acid with a pivaloyl halide (trimethylacetyl halide) in the presence of a base, such as pyridine, triethylamine, etc. Preparation of 5-hydroxy-5-(1-phenylethyl) barbituric acid is described in Belgian Pat. No. 775,117; it is provided by treating 5-(1-phenylethyl) barbituric acid with aqueous hydrogen peroxide in the presence of acetic acid. Pivaloyl chloride is a commercially available material; alternately it can be prepared by reacting the acid with excess thionyl chloride according to the process described by R. E. Kent and S. M. McElvain, *Org. Synth. Coll.* Vol. 3, p. 490 (1955). Pivaloyl bromide can also be synthesized according to the same procedure using thionyl bromide instead of thionyl chloride.

Preferably the preparation of the compound of this invention is carried out using an excess of base as a solvent. By "excess of base" is meant more than an equimolar amount of base. Optionally, an inert diluent can be employed as a co-solvent together with at least an equimolar amount of base. Suitable inert diluents include dimethyl formamide, dimethyl sulfoxide, dimethyl acetamide, hexamethylphosphoramide, etc.

Compound I is readily obtained in high yields and excellent purity, and is conveniently isolated from the reaction mixtures by techniques such as distillation, crystallization, preparative column chromatography, etc.

For this application, the compound can be formulated for oral or parenteral administration according to conventional techniques. Effectiveness and toxicity of this compound is such that each dosage unit can contain from 5 to 500 mg. of active material. Compositions for oral administration can be solid or liquid and can take the form of syrups, isotonic solutions, tablets, capsules etc. Suitable solid physiologically acceptable carriers include lactose, magnesium stearate, sucrose, talc, stearic acid, gelatin, polyvinyl pyrrolidone etc. Exemplary liquid physiologically acceptable carriers are peanut oil, olive oil, sesame oil and water. Furthermore, the carrier may include a time delay material such as glyceryl monostearate or glyceryl distearate, alone or in combination with a wax.

If a solid carrier is used, the preparation can be tabletted, placed in a hard gelatin capsule or in the form of a troche or lozenge. The amount of solid carrier will vary widely but preferably will be from about 25 mg. to about 1 gm. If a liquid carrier is used, the preparation may be in the form of a soft gelatin capsule, placed in an ampule or in a liquid suspension.

For parenteral administration, the carrier or excipient may be a sterile, parenterally acceptable liquid; e.g. water or a parenterally acceptable oil; e.g., arachis oil contained in ampules.

While any of the above compositions are efficacious, preferred are tablets for oral administration.

All tests were conducted on adult albino male mice (Charles River strain); the dosage consisted of the active agent suspended in 10% aqueous acacia and was administered orally and/or subcutaneously as indicated.

Acute oral toxicity was determined in the conventional manner. The results were expressed as $LD_{50}$, the dose required to produce death in 50% of the animals treated, determined graphically, with the 95% limits shown in parentheses.

Two established procedures were employed to determine analgetic activity. The method described by Eddy, N. B., and Leimbach, D., *J. Pharmacol. Exptl. Therap.* 107, 385 (1953) was followed, with the following modifications, in the first procedure. Mice are pretested by placing them individually on the cleaned surface of a copper water bath, the temperature of which is maintained at 54°–55°C. The reaction time of this noxious thermal stimulus is the time in seconds required for either licking of the paws or jumping, such that all four paws leave the surface of the plate. The drug is then administered orally or subcutaneously, generally at five dosage levels, (10 mice per dosage level) and the reaction times are redetermined at intervals of ½ hour, 1 hour, and 2 hours; the time of peak activity is the time at which the greatest number of animals is protected. From the pretreatment reaction times the mean and standard deviations are computed. The cut-off time is taken to be the mean reaction time plus 2 standard deviation units. Reaction times equal to or exceeding this cut-off time are considered to represent analgetic responses. The dosage required to produce an analgetic response in 50% of the animals ($ED_{50}$ and 95% limits) is computed graphically.

In the second procedure, the method of Siegmund, E., et al. reported in *Proc. Soc. Exptl. Biol. and Med.* 95, 729, (1957) was generally followed. The method is based on the antagonism by both non-narcotic and narcotic analgetics of a syndrome induced in mice following intraperitoneal injection of phenyl-p-quinone. The syndrome is characterized by intermittent contractions of the abdomen, twisting and turning of the trunk, and extension of the hind legs, beginning 3 to 10 minutes after the injection and persisting for more than one hour. The test drug is administered orally at four to five dosage levels. At the time of peak activity, 0.25 ml. of a 0.02 per cent solution of phenyl-p-quinone in 5 per cent (aqueous) ethyl alcohol is injected intraperitoneally. Inhibition of the syndrome is considered an analgetic response.

The following example will serve to illustrate the practice of this invention.

EXAMPLE

The amount of 5 g. of 5-hydroxy-5-(1-phenylethyl) barbituric acid, prepared following the procedure described in Belgian Pat. No. 775,117, was dissolved in a mixture of pivaloyl chloride (5 ml.) and 60 ml. pyridine. The mixture was heated at 75°C overnight, then cooled and poured into ice containing 60 ml. of concentrated hydrochloric acid. The product was extracted four times with ethyl acetate, and the combined extracts washed with saturated sodium chloride solution, sodium bicarbonate solution, dilute hydrochloric acid and sodium chloride solution. After drying over anhydrous sodium sulfate, solvent was removed by evaporation on a Buchi Rotovapor apparatus. The resulting product was purified by column chromatography (230 g. silica gel). Elution with 5% ethyl acetate in benzene solution followed by recrystallization from benzene provided 5-pivaloyloxy-5-(1-phenylethyl) barbituric acid, m.p. 205°–207°C.

Analysis — Calc'd for $C_{17}C_{20}O_5N_2$: C, 61.43; H, 6.07; N, 8.43. Found: C, 61.83; H, 6.04; N, 8.39.

Pharmacological testing of this compound gave the following results:

| | Dosage, mg/kg |
|---|---|
| Acute Toxicity | |
| $LD_{50}$ (oral) | 690(560–840) |
| Analgetic Activity | |
| Hot-Plate $ED_{50}$ (oral) | <3.1 |
| Hot-Plate $ED_{50}$ (subcutaneous) | (not dose-related) |
| | >40 <80 |
| Phenyl-p-quinone | (not dose-related) |
| Writhing | 26% active at 100 mg/kg |
| | 30% active at 200 mg/kg |
| | 10% active at 400 mg/kg |
| Therapeutic Index | |
| $LD_{50}/ED_{50}$ (oral) = >230 | |
| Time of Peak Activity | ½ hour |

What is claimed is:

1. A therapeutic composition for treatment of symptoms of pain in a warm-blooded animal comprising a physiologically acceptable carrier and an analgetically effective amount of 5-pivaloyloxy-5-(1-phenylethyl) barbituric acid.

2. A method of treating symptoms of pain in a warm-blooded animal which comprises administering to said animals an analgetically effective amount of a compound as claimed in claim 1.

* * * * *